US00PP08524P

United States Patent [19]

Trees

[11] Patent Number: Plant 8,524

[45] Date of Patent: Dec. 28, 1993

[54] GERANIUM PLANT 'DESIGNER ROSE'

[75] Inventor: Scott C. Trees, Nipomo, Calif.

[73] Assignee: Ball Floraplant, West Chicago, Ill.

[21] Appl. No.: 996,115

[22] Filed: Dec. 23, 1992

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 5,054 5/1983 Elsner ..... Plt. 87.12
P.P. 5,928 4/1987 Schumann ..... Plt. 87.12
P.P. 7,083 12/1989 Hofmann ..... Plt. 87.12

*Primary Examiner*—James R. Feyrer
*Attorney, Agent, or Firm*—Arnold, White & Durkee

[57] ABSTRACT

Geranium Designer Series TM Rose (BFP-142) is a new and distinct cultivar of geranium, botanically known as *Pelargonium* × *hortorum* Bailey, and hereinafter referred to by the cultivar name Designer Rose. Designer Rose was selected from a cross between the female parent Twist and the male parent Veronica. The new cultivar is distinguished from its parents and from other geraniums by its rose-purple color, high botrytis tolerance and basal branching spreading habit.

1 Drawing Sheet

BACKGROUND OF THE NEW PLANT

Designer Rose is a product of a planned breeding program which had the objective of creating new geranium cultivars with unique colors, large umbels, medium green foliage, weather tolerance, fast rooting and good shipping qualities.

Designer Rose was originated from a hybridization made in a controlled breeding program in West Chicago, Ill. The female parent was Twist (U.S. Plant Pat. No. 5,928), a semi-double coral with dark green foliage. The male parent of Designer Rose was Veronica (U.S. Plant Pat. No. 5,054), a semi-double dark purple with medium green foliage.

Designer Rose has 2.0–3.0 branches in a 10 cm pot, compared with approximately the same number for Veronica and poor branching (0–1.0) for Twist. Branching occurs without pinching for Designer Rose. Botrytis resistance is very good for both Veronica and Designer Rose. Botrytis resistance was not determined for Twist.

Designer Rose was discovered and selected as one flowering plant within the progeny of the stated cross by the inventor in a controlled environment in Santa Maria, Calif.

The first act of asexual reproduction of Designer Rose was accomplished when vegetative cuttings were taken from the initial selection in a controlled environment in Santa Maria, Calif. by a technician supervised by the inventor. Horticultural examination of selected units demonstrated that the combination of characteristics as herein disclosed for Designer Rose are firmly fixed and are retained through successive generations of asexual reproduction.

Designer Rose has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

The following traits have been repeatedly observed and are determined to be basic characteristics of Designer Rose which in combination distinguish this geranium as a new and distinct cultivar. These traits include basal branching without growth regulators, semi-double form, and the following listed characteristics.

Of the many commercial cultivars known to the present inventor, the most similar in comparison to Designer Rose is Fox (U.S. Plant Pat. No. 7,083). Designer Rose is similar in rose-purple color to Fox although tonality is somewhat different. Umbels are similar except that Designer Rose has fewer umbels per plant but a greater number of flowers per umbel. Designer Rose has semi-double corolla with 5–6 petals while Fox generally has 10–14 petals. Designer Rose grows taller by about 10 cm in the field and has a slightly larger corolla diameter than Fox. Fox has fair branching (1.5–2.5) in a 10 cm pot, whereas Designer Rose has 2.0–3.0 branches in a 10 cm pot and branching occurs without pinching. Compared to Designer Rose, Fox has generally poor resistance to Botrytis in the flowers. Both Fox and Designer Rose have stable flower color in full sun.

DESCRIPTION OF THE PHOTOGRAPH

The accompanying color photographs show a tip view of the typical flower and foliage characteristics of Designer Rose. The view taken against a dark background illustrates flower color closest to the color values assigned from The Royal Horticultural Society Color Chart. The view taken against a light background highlights the leaf characteristics.

DESCRIPTION OF THE PLANT

In the following description, color references are made to The Royal Horticultural Society Color Chart. The color values were determined between 10:00–11:00 a.m. on Nov. 10, 1992 under 600 foot candles at Arroyo Grande, Calif. USA.

Classification:

*Botanical.*—*Pelargonium* × *hortorum* Bailey.

*Commercial.*—Designer Rose, Zonal Geranium.

INFLORESCENCE

Umbel:

*Average diameter.*—8.5–9.0 cm.

*Average depth.*—6.5–7.0 cm.

*Peduncle length.*—10.5–11.0 cm.

*Pedicel length.*—2.0–2.5 cm.

*Number umbels/plant (designate circumstances)*-.—12 umbels/plant on 18 week old field grown plants.

*Number of flowers/umbel.*—23.

Corolla:

*Average diameter.*—4.5–4.7 cm.

*Form.*—Semi-double with 5–6 petals.

*Length.*—2.5–2.7 cm.

*Width.*—1.5–2.0 cm.

*Number of petaloids.*—2–3. length: 2.0–2.2 cm; width: 1.5–1.8 cm.

*Appearance.*—Upper 2–3 petals have distinct pattern of 3 colors Background and upper ⅔ of petal is rose-purple (57A), the middle of the petal is red-purple (63A), and the bottom petal attachment area is red group 53A.

*Flower color stability.*—Stable in full sun.

*Bloom.*—Continuous bloom-does not require removal of spent flowers to keep flowering.

*Color (General tonality from a distance of three meters).*—Rose-Purple 57A.

*Description of petal form.*—Non-imbricate.

*Color (abaxial).*—57A.

*Color (adaxial).*—58C.

Bud:

*Shape.*—Oval.

*Color (abaxial).*—57A.

*Color (adaxial).*—57B.

Reproductive organs:

*Androecium.*—Seven 10–12 mm anther/filaments, 2.0 mm anther.

*Gynoecium.*—9 mm, 5–6 lobed stigma, 4 mm style.

*Presence or absence of fruits.*—No fruits.

Spring flowering response period: 7–8 weeks from unrooted cutting.

Outdoor flower production: Freely flowering.

Durability: High Botrytis resistance.

Foliage:

*Leaf size (mature leaves).*—10.0–11.0 cm at widest area; 6.0–6.5 cm at narrowest area.

*Leaf stem.*—6.1–7.0 cm length.

*Zonation.*—Very slight in greenhouse; darker under field grown conditions.

*Form.*—Reniform, cordate.

*Margin.*—Crenate.

*Color (abaxial).*—137A leaf margin; 137B leaf base.

*Color (adaxial).*—137C.

*Color (zonation).*—Slight.

*Tolerance of botrytis.*—Good.

General appearance and form:

*Internode length.*—0.5–1.0 cm.

*Branching pattern.*—Basal branching, spreading.

*Height.*—33.02 cm on 18 week old field grown plants.

What is claimed is:

1. A new and distinct geranium cultivar, substantially as herein described and shown, characterized by its rose-purple color, botrytis tolerance and basal branching in the absence of growth regulators.

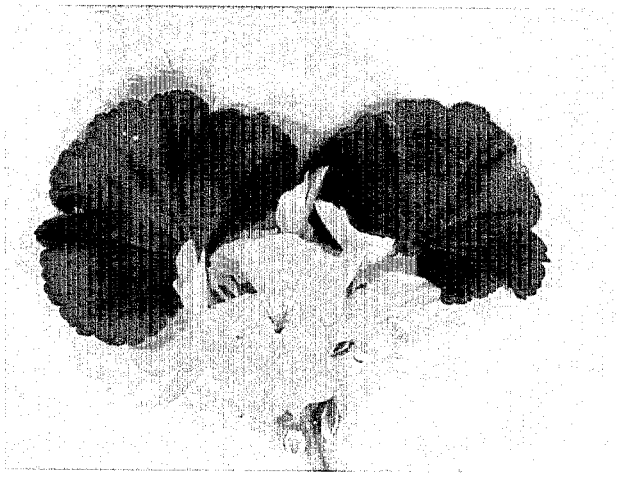
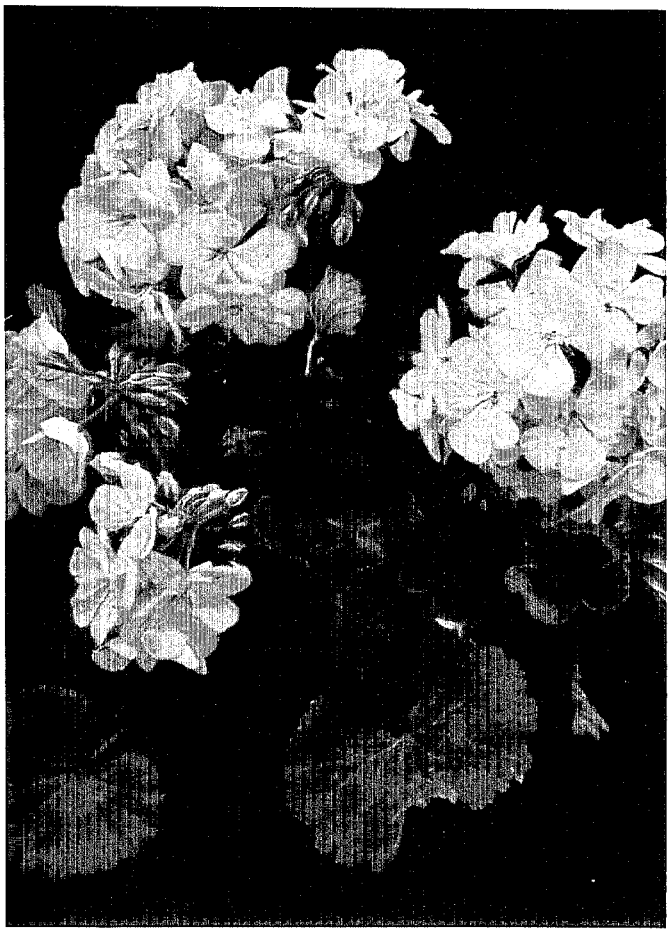

* * * * *